June 8, 1954 A. VUYK Plant Pat. 1,283
AZALEA PLANT
Filed July 24, 1953
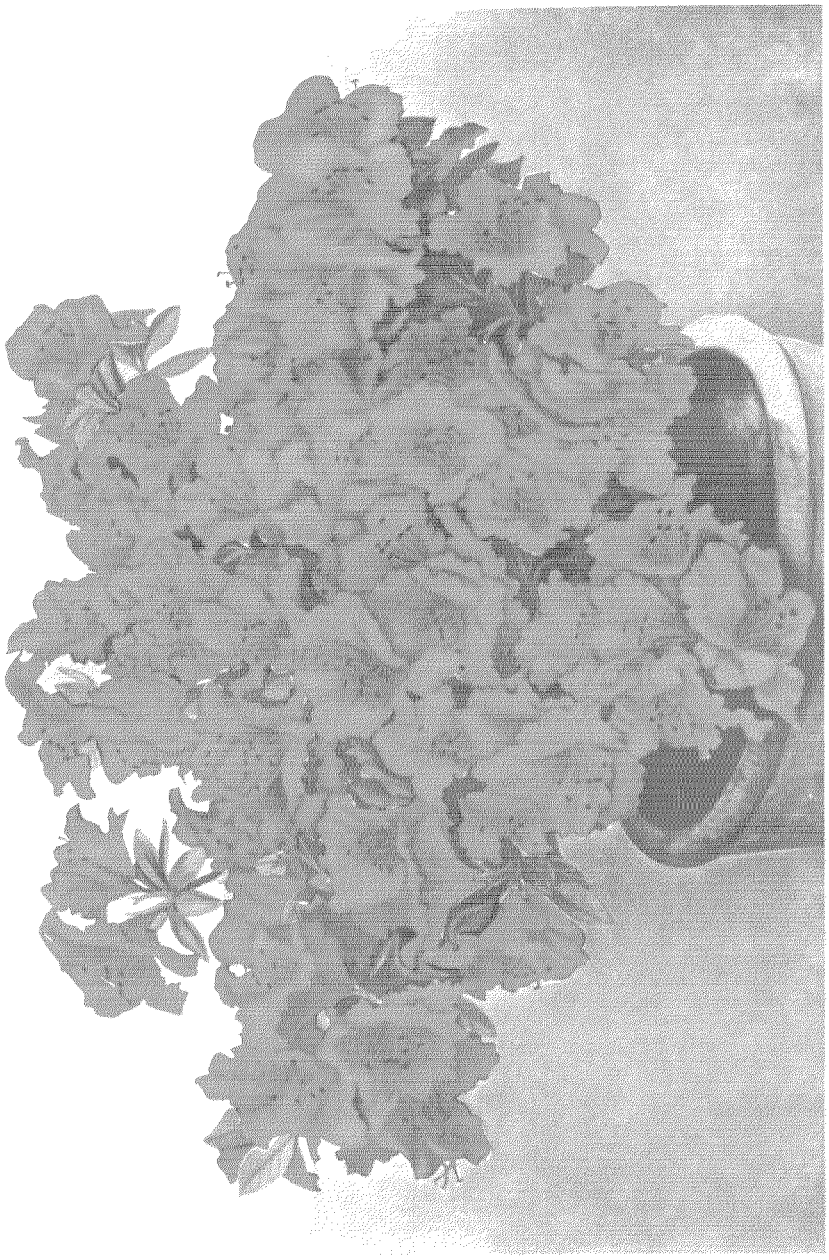
Inventor:
Aart Vuyk
By Cobb & Robb
attorneys.

Patented June 8, 1954 Plant Pat. 1,283

UNITED STATES PATENT OFFICE 1,283

AZALEA PLANT

Aart Vuyk, Boskoop, Netherlands, assignor to Vuyk Van Nes, Boskoop, Netherlands, a partnership Application July 24, 1953, Serial No. 370,241

1 Claim. (Cl. 47—60)

The present invention relates to a new and distinct variety of azalea plant which was originated by me by crossing two unnamed and unpatented varieties which are identified in my breeding records by the following designations:

Seed parent: VVN 128 (derived from crossing an unnamed hardy *Azalea vuykiana* seedling × *Azalea macrantha* Red.)

Pollen parent: VVN 1 (derived from crossing an unnamed hardy *Azalea vuykiana* seedling × *Azalea indica* Apollo).

As the result of this breeding, I have produced a new variety of azalea plant which is distinguished from its parents, as well as from all other varieties of its class of which I am aware, as evidenced by the following unique combination of outstanding characteristics:

(1) The radiant scarlet general color tonality of the flowers, which is a distinctly new color in the hardy azalea world, and which is the most outstanding and most valuable characteristic of my new variety;

(2) Absence of fading of the flowers when exposed to the sun;

(3) The unique bearing habit of the flowers which stand firmly and straight up on the stems and which better expose the inside of the flower which is the most brilliant part thereof, as distinguished from the drooping habit of the flowers in most other large flowering azaleas; and (4) The free formation of flower buds on nearly every branch, resulting in an abundance of flowers in the spring.

Asexual reproduction of my new variety by cuttings at Boskoop, Holland, shows that the foregoing characteristics and distinctions come true to form and are established and transmitted through succeeding propagations.

The accompanying drawing shows a typical specimen plant of my new variety, as depicted in color, and with the flowers in various stages of development, the color of the latter being as nearly true as it is reasonably possible to make the same in a color illustration of this character.

The following is a detailed description of my new variety as based upon observations made in Boskoop, Holland, with color terminology in accordance with Robert F. Wilson's Horticultural Colour Chart, as issued by the British Color Council in collaboration with the Royal Horticultural Society, except where general color terms of ordinary dictionary significance are obvious.

Type: Hardy; evergreen.

Parentage: Seedling.

*Seed parent.*—An unnamed azalea designated as VVN 128.

*Pollen parent.*—An unnamed azalea designated as VVN 1.

*Plant*

Form of plant: Bush; much-branched; compact.

Growth habit: Medium; branching; compact.

Rooting: Vigorous; compact.

Blooming habit: Forms flower buds freely, resulting in profusion of blooms.

Blooming season: May.

Suitability for forcing: Excellent for Easter season forcing.

Foliage:

*Size.*—Medium.

*Quantity.*—Abundant.

*Color.*—New foliage: Under side—Fern Green, Plate 086; under side—Pod Green, Plate 061/2. Old foilage: Upper side—Parsley Green, Plate 00962; under side—Fern Green, Plate 0862/1.

*Shape.*—Oval pointed.

*Texture.*—Upper side—Glossy. Under side—Rough.

*Edge or margin.*—Smooth.

*Aspect.*—A commercially valuable and desirable evergreen hybrid azalea of compact form, with glossy leaves which are deep green color in summer and having a reddish green tint in fall and winter, and which is particularly characterized by its abundant production of brilliant scarlet flowers in spring.

*Disease resistance.*—Similar to that of hardy Vuykiana azaleas such as "Wilhelmina Vuyk," "Gerardina Vuyk" and "Beethoven," all unpatented, as determined by comparison with these varieties growing under comparable cultural conditions at Boskoop, Holland.

*Flower*

Flowers borne: 2 to 4 to stem; in clusters; on strong, medium length stems.

Quantity of bloom: Abundant, both outdoors and in greenhouse.

Continuity: One season. Permanence—3 to 4 weeks; non-fading in sun.

Petalage:

*Number of petals under normal conditions.*—4 to 6, but generally 5.

*Color of bud.*—Crimson, Plate 22.

*Color of open flower.*—From Scarlet, Plate 19 to Cherry, Plate 722.

*Texture.*—Firm; crisp.

*Appearance.*—Inside—Scarlet, Plate 19 to Cherry, Plate 722. Outside — Crimson, Plate 22.

*Shape.*—Medium depth; fringed edges; from 2½ to 3 inches in diameter.

*Arrangement.*—In clusters of generally 3 to 4 flowers which stand firmly straight up.

*Reproductive organs*

Stamens: 7 to 10 per flower. Color—Crimson, Plate 22.

Pollen: Color—Aureolin, Plate 3/3.

Styles: 1 per flower.

Ovaries: Four.

I claim:

A new and distinct variety of azalea plant of the hardy evergreen type, substantially as herein shown and described, characterized particularly as to novelty by the radiant scarlet general color tonality of its flowers, by the absence of fading of the flowers when exposed to the sun, by the erect and firm bearing habit of the flowers, and by the freedom of production of flower buds on nearly every branch, with resulting abundance of blooms during the blooming season.

No references cited.